(12) United States Patent
Bosch et al.

(10) Patent No.: US 6,420,537 B1
(45) Date of Patent: Jul. 16, 2002

(54) MACROLIDE PRODUCTION

(75) Inventors: Immaculada Bosch, Vic; Victor Centellas, Cardedeu; José Diago, Granollers, all of (ES)

(73) Assignee: Biochemie S.A., Barcelona (ES)

( * ) Notice: Subject to any disclaimer, the term of this patent is extended or adjusted under 35 U.S.C. 154(b) by 0 days.

(21) Appl. No.: 09/707,566

(22) Filed: Nov. 7, 2000

Related U.S. Application Data

(63) Continuation of application No. PCT/EP99/03134, filed on May 6, 1999.

(30) Foreign Application Priority Data

| May 8, 1998 | (GB) | ............................................... 9809939 |
| Jun. 12, 1998 | (GB) | ............................................... 9812743 |

(51) Int. Cl.⁷ ................................................. C07H 1/00
(52) U.S. Cl. ....................................... 536/7.4; 536/18.5
(58) Field of Search ................................. 536/7.4, 18.5

(56) References Cited

U.S. PATENT DOCUMENTS 4,517,359 A   5/1985   Kobrehel et al.

FOREIGN PATENT DOCUMENTS

| EP | 0 101 186 | 11/1986 |
| EP | 0 109 253 | 10/1987 |
| EP | 0 298 650 | 2/1992 |
| EP | 0 508 725 A1 | 10/1992 |
| EP | 0 467 331 | 11/1995 |
| EP | 0 827 965 A2 | 3/1998 |
| EP | 0 879 823 | 11/1998 |

OTHER PUBLICATIONS

Jones, A. Brian, "New Macrolide Antiboitics: Synthesis of a 14–membered azalide, " J. Org. Chem., vol. 57, pp. 4361–4367 (1992).

Vajtner, Z. et al., "Kinetics of the Azithromycin Synthesis from Azaerythromycin by HPLC method, " Kem. Ind., vol. 43(6), pp. 283–286 (1994) [Original (Croatian) with English Translation].

Vajtner et al., Kem. Ind., vol. 43 (6) pp. 283–286 (1994).

*Primary Examiner*—Elli Peselev
(74) *Attorney, Agent, or Firm*—Hesna J. Pfeiffer

(57) ABSTRACT

A process for the production of azithromycins by methylation of the nitrogen atom in position 9 of the ring structure in 9-deoxo-9a-aza-9a-homoerythromycins in the presence of formaldehyde and in the presence of a reducing agent in non-halogenated solvent; and azithromycin which is free from halogenated organic solvent in a stable anhydrous form; or in the form of a solvate with non-halogenated solvent with the exception of water.

3 Claims, No Drawings

MACROLIDE PRODUCTION

This application is a continuation of International Application No. PCT/EP99/03134, filed May 6, 1999, the contents of which are incorporated herein by reference.

This present invention relates to azithromycins, e.g. a compound of formula

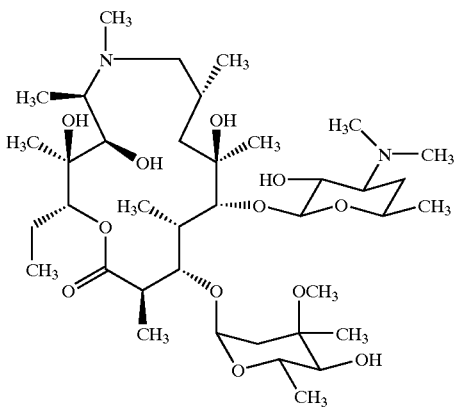

I

Azithromycin (9-deoxo-9a-aza-9a-methyl-9a-homoerithromycin A) is a well-known antibacterial agent described e.g. in The Merck Index, 12th Edition (1996), page 157 (946).

An azithromycin or azithromycins as used herein includes azithromycin of formula I and a compound of formula I, wherein one or more free hydroxyl groups are substituted, e.g. by protecting groups; e.g. conventional hydroxy protecting groups; and/or a methoxy group is replaced by a free hydroxyl group or by a hydroxyl group which is substituted excluding methoxy, e.g. by protecting groups, e.g. conventional hydroxy protecting groups; and/or a dimethylamino group is replaced by a substituted amino group excluding dimethylarnino, e.g. by a protected amino group, e.g. a conventional protected amino group.

Azithromycins, e.g. azithromycin of formula I, may e.g. be produced by methylation e.g. by a method as conventional, of 9-deoxo-9a-aza-9a-homoerythromycins, e.g. 9-deoxo-9a-aza-9a-homoerythromycin, e.g. a compound of formula

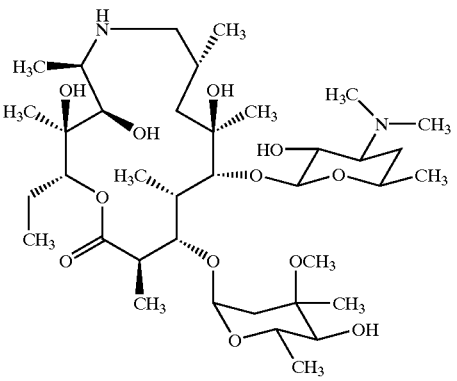

II e.g. via an Eschweiler-Clarke reaction, e.g. in the presence of formaldehyde and in the presence of a reducing agent, e.g. formaldehyde/formic acid, in halogenated solvent, A 9-deoxo-9a-aza-9a-homoerythromycin or 9-deoxo-9a-aza-9a-homoerythromycins as used herein include a compound of formula II and a compound of formula II, wherein one or more free hydroxyl groups are substituted, e.g. by protecting groups; e.g. conventional hydroxy protecting groups; and/or a methoxy group is replaced by a free hydroxyl group or by a hydroxyl group which is substituted excluding methoxy, e.g. by protecting groups, e.g. conventional hydroxy protecting groups; and/or a dimethylamino group is replaced by a substituted amino group excluding dimethylamino, e.g. by a protected amino group, e.g. conventional protected amino group.

9-deoxo-9a-aza-9a-homoerythromycins are known and obtainable e.g. by a method as conventional.

It was now surprisingly found, that an Eschweiler-Clarke reaction in the production of azithromycins starting from 9deoxo-9a-aza-9a-homoerythromycins including methylation and isolation of azithromycins, e.g. a compound of formula I, may be carried out avoiding halogenated solvent.

In one aspect the present invention provides a process for the production of azithromycins, e.g. azithromycin, e.g. of formula I, by methylation of the nitrogen atom in position 9 of the ring structure in 9-deoxo-9a-aza-9a-homoerythromycins, e.g. a compound of formula II, in the presence of formaldehyde and in the presence of a reducing agent, e.g. formic acid or hydrogen, comprising that methylation, e.g. and isolation of azithromycins, is carried out in non-halogenated solvent, e.g. selected from water, alcohols, ketones, alkyl esters and ethers.

A process according to the present invention may be carried out as follows: The nitrogen atom in position 9 of the ring structure in 9-deoxo-9a-aza-9a-homoerythromycins may be methylated in the presence of formaldehyde and in the presence of a reducing agent in non-halogenated solvent.

A hydroxyl protecting group in 9-deoxo-9a-aza-9a-homoerythromycins includes e.g. conventional hydroxyl protecting groups, including e.g. protecting groups for the diol function present in positions 11 and 12 of a compound of formula II, such as protecting groups which form a cyclic group together with two hydroxy groups, e.g. a hydrogenorthoborate group.

Non-halogenated solvent includes e.g. water and an organic solvent, the chemical formula of which does not contain halogen atoms. In contrast to that, halogenated solvent includes organic solvent, the chemical formula of which contains at least one halogen atom.

Non-halogenated solvent as used herein includes solvent which is miscible with water and solvent which is able to form a two phase system with water, including, e.g. a solvent of a low dielectric constant, e.g. appropriate ketones, such as dialkyl ketones, e.g. for example di($C_{1-5}$)alkylketones, e.g. methyl-($C_{1-5}$)alkyl ketones, e.g. acetone and methylisobutyl ketone; di-($C_{2-5}$) alkyl ketones, such as diethylketone and diisopropylketone; esters, such as alkanoic acid esters, e.g. ($C_{1-6}$)alkanoic acid, e.g. acetic acid alkyl, e.g. ($C_{1-8}$) alkyl, such as $(C_{1-6})$alkyl, e.g. $(C_{1-4})$alkyl esters, for example n-butyl acetate, isopropyl acetate and ethyl acetate; ethers such as cyclic ethers, e.g. tetrahydrofuran and non-cyclic, e.g. dialkyl ethers, such as di$(C_{1-8})$alkyl, e.g. di$(C_{1-4})$alkyl ethers, such as methyl$(C_{1-4})$alkyl ethers, e.g. t-butyl methyl ether; and aromatic hydrocarbons, such as xylene or toluene; and solvents of higher dielectric constant, e.g. alcohols, such as alkyl alcohols, e.g.$(C_{1-5})$alkyl alcohols, for example methanol, ethanol and isopropanol; and amides, e.g. derived from a carboxylic acid, such as an alkanoic acid, , e.g. $(C_{1-3})$alkanoic acid, and including monoalkyl- and dialkylamides; e.g. mono$(C_{1-4})$alkyl and di$(C_{1-4})$alkylamides, such as N-methylformamide, dimethylacetamide and dimethylformamide.

Preferred non-halogenated solvents includes solvents, with low toxicity, e.g. pharmaceutically acceptable solvents, for example water; and alcohols such as ethanol, isopropanol and butanols; ketones such as acetone, methyl ethyl ketone and methyl isobutyl ketone; alkyl esters such as formic acid and acetic acid esters, e.g. ethyl acetate, isopropyl acetate and butyl acetate and ethers such as tert-butyl methyl ether and tetrahydrofuran, more preferably alcohols, esters, e.g. acetates, ketones and water. Non-halogenated solvent includes a solvent system, e.g. mixtures of individual solvents, e.g. as described above.

A solution of 9-deoxo-9a-aza-9a-homoerythromycins in a non-halogenated organic solvent as used as starting material according to the present invention may contain, e.g. a small amount of, water, e.g. to facilitate dissolution of 9-deoxo-9a-aza-9a-homoerythromycins, e.g. in case that 9-deoxo-9a-aza-9a-homoerythromycins in the form of a salt are used as a starting material.

If not otherwise defined herein alkyl includes $(C_{1-12})$ alkyl, such as $(C_{1-6})$alky, for example $(C_{1-4})$alkyl. Lower alkyl includes e.g.$(C_{1-4})$alkyl. Formaldehyde according to the present invention as used herein includes formaldehyde, e.g. in the form of a gas, formaldehyde in aqueous and in non-halogenated solvent, e.g. as described above, solution and a formaldehyde precursor. A formaldehyde precursor includes a compound which may set free formaldehyde in an reaction medium, such as paraformaldehyde or s-trioxane. If a non-halogenated solvent is water, formaldehyde in a molar excess (in respect with a 9-deoxo-9a-aza-9a-homoerythromycins A used as a starting material) in form of an aqueous solution may be used, e.g. without use of further water.

A reducing agent according to the present invention as used herein includes conventional reducing agents useful in a reductive alkylation process, such as formic acid, zinc/HCI, sodium cyanoborohydride, sodium triacetoxyborohydride, sodium borohydride, $BH_3$-pyridine, formic acid and hydrogen, e.g. in the presence of a, e.g. conventional, hydrogenation catalyst. A preferred reducing agent includes e.g. formic acid and hydrogen in the presence of a hydrogenation catalyst.

The amounts of formaldehyde and of the reducing agent present in the methylation reaction according to the present invention are not critical; e.g. a stoechiometric amount or more relating to a 9-deoxo-9a- aza-9a-homoerythromycin A starting compound may conveniently be present. An appropriate amount includes e.g. 1 to 30, such as 1 to 5, e.g. 1 to 3 equivalents of formaldehyde and of a reducing agent. Appropriate reaction conditions for the methylation reaction according to the present invention include e.g.

a temperature range of ca $-10°$ C. up to the reflux temperature of the solvent or solvent system present, such as from $30°$ C. to $80°$ C., e.g. more than 50C.;

an appropriate pressure, e.g. atmospheric pressure, and a pressure which is above or below atmospheric pressure; and appropriate dilution, e.g. a dilution range between 1 g and 1000 g of a 9-deoxo-9a- aza-9a-homoerythromycin A starting compound per liter of non-halogenated solvent.

A compound of formula I or a compound of formula I wherein one or more free hydroxyl groups are substituted, e.g. by protecting groups; e.g. conventional hydroxy protecting groups; and/or a methoxy group is replaced by a free hydroxyl group or by a hydroxyl group which is substituted excluding methoxy, e.g. by protecting groups, e.g. conventional hydroxy protecting groups; and/or a dimethylamino group is replaced by a substituted amino group excluding dimethylamino, e.g. by a protected amino group, e.g. conventional protected amino group, may be formed and may be isolated from the reaction mixture, e.g. as conventional, e.g. by removal of solvent from the reaction mixture, e.g. by concentration such as evaporation, e.g. to dryness or almost dryness, e.g. until crystallisation or precipitation of an azithromycin, e.g. of formula I, occurs; or by extraction, e.g as a salt, e.g. into an aqueous solution of acidic pH; and precipitation, e.g. as a salt from an aqueous medium; or extraction at basic pH into another non-halogenated solvent, e.g. as defined above, which may be the same or different from that used in methylation; and precipitation or crystallizitaion of an azithromycin, e.g. of formula I.

If a compound of formula I, wherein one or more free hydroxyl groups are substituted, e.g. by protecting groups; e.g. conventional hydroxy protecting groups; and/or a methoxy group is replaced by a free hydroxyl group or by a hydroxyl group which is substituted excluding methoxy, e.g. by protecting groups, e.g. conventional hydroxy protecting groups; and/or a dimethylamino group is replaced by a substituted amino group excluding dimethylamino, e.g. by a protected amino group, e.g. conventional protected amino group, is formed, this compound may be converted into a compound of formula I, e.g. using e.g. a method as conventional, e.g.

de- and/or reprotecting one or more hydroxyl groups; and/or producing a methoxy group e.g. by methylation of an hydroxy group; and/or producing a dimethylamino group e.g. by de- and or realkylation to obtain a compound of formula I.

In another aspect the present invention provides a process for the production of azithromycin, e.g. of formula I, by methylation of the nitrogen atom in position 9 of the ring structure in 9-deoxo-9a-aza-9a-homoerythromycins, e.g. a compound of formula II, in the presence of formaldehyde and in the presence of a reducing agent, e.g. formic acid or hydrogen, and, e.g. if necessary, converting a 9-deoxo-9a-aza-9a-methyl-9a-homoerithromycin A into a compound of formula I, comprising that methylation, e.g. and isolation of a compound of formula I, is carried out in non-halogenated solvent, e.g. selected from water, alcohols, ketones, alkyl esters and ethers.

In a process according to the present invention high yields may be obtained, for example, methylation may result in a yield higher than 90% or even more, e.g. higher than 95%;

and reaction times may be short, e.g. shorter than 4 hours, such as 2 hours. A process according to prior art, e.g. in halogenated solvent, may e.g. result in lower yields and e.g. higher reaction times.

9-deoxo-9a-aza-9a-methyl-9a-homoerythromycin A, e.g. of formula I obtained according to the present invention is useful, e.g. for the production of a pharmaceutical composition; and, if necessary may be converted into a suitable form for pharmaceutical administration, e.g. into the form of a, e.g. pharmaceutically acceptable salt, and/or e.g. into the form of a solvate, e.g. a hydrate such as a monohydrate or a dihydrate. A dihydrate of a compound of formula I may be e.g. obtained by a method as conventional, such as by crystallisation of a compound of formula I, e.g. in acetone/water or by crystallisation in a mixture of aqueous tetrahydrofuran and hexane. Azithromycin in the form of a monohydrate may be obtained, e.g. as conventional, e.g. by crystallization of azithromycin in ethanol/water.

A compound of formula I may be obtained in the form of a solvate with non-halogenated solvent.

In a further aspect, the present invention provides a process for the production of azithromycin, e.g. of formula I, in the form of a solvate, by methylation of the nitrogen atom in position 9 of the ring structure in 9-deoxo-9a-aza-9a-homoerythromycins in the presence of formaldehyde and in the presence of a reducing agent, e.g. formaldehyde or hydrogen, and, if necessary, converting a 9-deoxo-9a-aza-9a-methyl-9a-homoerithromycin A obtained into a compound of formula I, and, converting a compound of formula I into e.g. a salt and/or, a solvate thereof, comprising that methylation, e.g. and isolation of azithromycin, is carried out in non-halogenated solvent e.g. selected from water, alcohols, ketones, alkyl esters and ethers.

In another aspect the present invention provides a process for the production of a pharmaceutical composition comprising azithromycin in e.g. pharmaceutically acceptable salt form or, free form, e.g. in the form of a solvate, in association with at least one pharmaceutical carrier or diluent wherein azithromycin is obtained by a process according to the present invention.

The process according to the present invention may e.g. have advantages as follow:

Azithromycin, e.g. of formula I, e.g. in the form of a solvate, may be obtained without the use of halogenated solvents Azithromycin, e.g. of formula I, e.g. in the form of a solvate may be obtained in high yields and short reaction times.

In another aspect surprisingly a process for the production of azithromycin in non-halogentated organic solvent with the exception of water as a solvent was found which provides anhydrous azithromycin in a stable, e.g. non-hygroscopic, form and practically free from halogenated organic solvent.

The term "free from halogenated organic solvent" used herein, includes e.g. traces of halogenated solvents in azithromycin according to the present invention, such as amounts of 60 ppm and below, e.g. 2 to 60 ppm, or even less.

A stable, e.g. non-hygroscopic, anhydrous form of azithromycin includes a compound of formula I which is practically free from halogenated solvent and having and maintaining a water content of (about) 0.1% to 2.0%, such as 0.2% to 0.9% under normal environment air humidity conditions, e.g. for at least 24 hours, e.g. for several weeks.

In another aspect the present invention provides azithromycin, e.g. of formula I, which is free from halogenated organic solvent in a stable, e.g. non-hygroscopic, anhydrous form, e.g. having, e.g. and maintaining, a water content of 0.2% to 0.9%, e.g. under normal environment air humidity conditions, e.g. for, e.g. at least, 24 hours.

Azithromycin in a stable anhydrous form, which is free from halogenated organic solvent according to the present invention may be produced e.g. by producing a solution of azithromycin in a non-halogenated organic solvent with the exception of water as a solvent, e.g. drying said solution, and isolating and drying a composition containing azithromycin and non-halogenated organic solvent; e.g. directly by an Eschweiler-Clark reaction starting from 9-deoxo-9a-aza-9a-homoerythromycin, e.g. as described above.

For the production of a solution of azithromycin in a non-halogenated organic solvent with the exception of water as a solvent as used as starting material according to the present invention azithromycin in any form may be used, e.g. in free base form and in the form of a salt; e.g. in non-solvate form, e.g. anhydrous form, and/or in the form of a solvate. A salt includes e.g. preferably a hydrochloride, dihydrochloride, acetate, sulphate. A solvate includes a hydrate, such as a monohydrate and a dihydrate. If a salt of azithromycin is used as a starting material, a base, including e.g. inorganic bases such as sodium and potassium hydroxide, may be used, e.g. may be added to the solution, to provide azithromycin in free base form, e.g. by adjustment of the pH of the solution to an pH where azithromycin is present in free base form, including e.g. a pH range of 7 to 11. The concentration of azithromycin in a solution of a non-halogenated organic solvent is not critical. E.g. for ecological reasons preferably a saturated or almost saturated solution may be used. The temperature for the production of a solution of azithromycin in a non-halogenated organic solvent with the exception of water as a solvent includes a temperature at which azithromycin is not degraded including e.g. a temperature range of e.g. ca. 0° C. to ca. 30° C., such as 0 to 30° C.

Preferred non-halogenated solvents with the exception of water as a solvent include pharmaceutically acceptable solvents, for example alcohols such as ethanol, isopropanol or butanol; ketones such as acetone, methyl ethyl ketone or methyl isobutyl ketone; alkyl esters such as formate or acetate esters, e.g. ethyl acetate, isopropyl acetate or butyl acetate and ethers such as tert-butyl methyl ether or tetrahydrofuran.

A solution of azithromycin in a non-halogenated organic solvent with the exception of water as a solvent may be dried e.g. as conventional, e.g. by addition of a drying agent, such as anhydrous sodium or magnesium sulphate or a molecular sieve. For the isolation of azithromycin in anhydrous form according to the present invention the organic solvent of a solution of azithromycin in a non-halogenated organic solvent with the exception of water as a solvent may be removed, e.g. by distillation, such as vacuum distillation. Solvent may be removed partially, e.g. until azithromycin in anhydrous form crystallizes or precipitates or (almost) totally, e.g. to dryness. A composition containing azithromycin in anhydrous form and non-halogenated solvent, e.g. 10% and less, such as ca. 1% to 10%, e.g. 1% to 7%; may be obtained. In some cases, e.g. if the solution of azithromycin in non-halogenated solvents contains acetates, alcohols or ethers, azithromycin in the form of a solvate, e.g. crystalline, with non-halogenated solvent may be obtained.

In another aspect the present invention provides
  a composition containing azithromycin of formula I and, in an amount of 10% and less, a non-halogenated organic solvent with the exception of water and ethanol as a solvent; and, in a further aspect, azithromycin of formula I in the form of a solvate with non-halogenated organic solvent with the exception of water as a solvent.

A composition containing azithromycin in anhydrous form and non-halogenated solvent with the exception of water as a solvent, e.g. in the form of a solvate with non-halogenated solvent, may be dried to obtain azithromycin in anhydrous, e.g. in non-hygroscopic, form and free from halogenated solvents. Appropriate drying temperatures includes a temperature of ca. 40° C. and more, such as 40° C. to 65° C., e.g. 55° C. to 65° C. An appropriate drying time may be used, including for example more than 6 hours, e.g. overnight or more, e.g. 10 to 20 hours, such as 12 to 16 hours. Anhydrous azithromycin obtained according to the present invention may be non-hygroscopic, e.g. it may maintain a water content below the stoechiometric amount of the monohydrate of 2.3 %, for example below 2 %, e.g. below 1%, e.g. between 0.2 to 0.9%, such as 0.4 to 0.8% even after several hours, e.g. 24 hours, or several weeks, under normal, e.g. normal air humidity, environmental conditions.

Azithromycin which is free from halogenated organic solvent in a stable anhydrous form according to the present invention may be obtained in high purity of 95% and more, e.g. 95% to ca. 98%.

In another aspect the present invention provides a process for the production of azithromycin which is free from halogenated organic solvent in a stable anhydrous form, comprising producing a solution of azithromycin in a non-halogenated solvent with the exception of water as a solvent, e.g. and drying a solution of azithromycin in a non-halogenated solvent, and isolating and drying a composition containing azithromycin and non-halogenated solvent with the exception of water as a solvent.

Azithromycin which is free from halogenated organic solvent in a stable anhydrous form, e.g. and azithromycin in the form of a solvate with non-halogenated solvent with the exception of water as a solvent, according to the present invention is useful for the production of a pharmaceutical composition containing azithromycin. A pharmaceutical composition containing azithromycin which is free from halogenated organic solvent in a stable anhydrous form, e.g. and azithromycin in the form of a solvate with non-halogenated solvent with the exception of water as a solvent, may contain the same concentrations of azithromycin and may be used for the same indications in the same dosages as a known pharmaceutical composition containing azithromycin in the form of a monohydrate or dihydrate, e.g. as is presently on the market.

In another aspect the present invention provides a pharmaceutical composition, comprising a therapeutically effective amount of azithromycin which is free from halogenated organic solvent in a stable anhydrous form in association with at least one pharmaceutical carrier or diluent; and
- a pharmaceutical composition, comprising a therapeutically effective amount of azithromycin in the form of a solvate with non-halogenated solvent with the exception of water as a solvent in association with at least one pharmaceutical carrier or diluent.

The following examples illustrate the invention. All temperatures are in degree Centigrade and are uncorrected. The content of azithromycin in stable anhydrous azithromycin obtainable according to the examples is calculated by HLC on anhydrous basis. Azithromycin used as starting material is obtained by know methods or by a method according to the present invention.

EXAMPLES 1 to 9

General Reaction Procedure 0.55 g of 9-deoxo-9a-aza-9a-homoerythromycin A dissolved in 6 ml of a solvent as specified in TABLE 1 below under "Solvent" are treated at room temperature with 0.063 ml of formic acid (98–100%) and 0.135 ml of 37–38% w/w aqueous formaldehyde. In example 9 instead of 6 ml of "Solvent" and instead of 0.135 ml of 37–38% w/w aqueous formaldehyde, 3.9 ml of 37–38% w/w aqueous formaldehyde are used. The reaction mixture is heated at a temperature as specified in TABLE 1 below under "Temperature (in ° Celsius)". Within the time as specified in TABLE 1 below under "Time (in hours)" a conversion of 9-deoxo-9a-aza-9a-homoerythromycin A into azithromycin as specified in TABLE 1 under "Conversion (in % of starting material)" is determined by HPLC.

TABLE 1

| Example | Solvent | Temperature | Time | Conversion |
| --- | --- | --- | --- | --- |
| 1 | iso-propanol | 65–70 | 4 | 95 |
| 2 | 2-butanol | 70 | 2 | not determined |
| 3 | iso-propyl acetate | 70 | 2 | not determined |
| 4 | n-butyl acetate | 70 | 2 | not determined |
| 5 | ethyl acetate | 70 | 2 | not determined |
| 6 | acetone | 65–70 | 2 | 94 |
| 7 | iso-butyl ketone | 65–70 | 2 | 73 |
| 8 | toluene | 65–70 | 2 | 62 |
| 9 | water | 70 | 4.5 | 63 |

EXAMPLE 10

General Isolation Procedure (Solvent Soluble in Water)

A reaction mixture obtained as described in Example 1 is cooled to room temperature and the solvent is removed by evaporation.

0.52 g (92% of theory) of azithromycin are obtained.

Such an isolation procedure may be convenient in case that water soluble solvent is used.

EXAMPLES 2a to 5a

General Isolation Procedure (Solvent May Form a Two Phase System With Water)

A reaction mixture as obtained in one of the Examples above as specified in TABLE 2 below under "Reaction Example" is cooled to room temperature and treated with 40 ml of solvent as specified in TABLE 2 below under "Solvent", 40 ml of water and 20% sulfuric acid to obtain a pH of the mixture of ca. 4. The mixture obtained is stirred for ca. 15 minutes and the phases are separated. The aqueous phase obtained is extracted with 25 ml of solvent as specified in TABLE 2 below under "Solvent". The aqueous phase is treated with 20% sodium hydroxide to obtain a pH 9 and the mixture obtained is stirred for ca. 15 minutes and extracted with 25 ml of solvent as specified in TABLE 2 below under "Solvent". The organic phase is dried over anhydrous sodium sulphate and the sodium sulphate is filtrated off. The organic solvent is evaporated off.

Azithromycin in a yield as specified in TABLE 2 below under "Yield (in gram)" in % of theory as specified in TABLE 2 below under "% of theory" is obtained.

TABLE 2

| Example | Reaction Example | Solvent | Yield | % of theory |
|---|---|---|---|---|
| 2a | 2 | 2-butanol | 0.51 | 90 |
| 3a | 3 | iso-propyl acetate | 0.46 | 82 |
| 4a | 4 | n-butyl acetate | 0.50 | 89 |
| 5a | 5 | ethyl acetate | 0.54 | 96 |

EXAMPLE 11–18

General Procedure For Obaining Azithromycin in Stable, Anhydrous Form

Azithromycin is dissolved in a solvent as specified in TABLE 3 below. Anhydrous sodium sulphate is added to 100 ml of a solution of azithromycin in a solvent as specified in TABLE 3 below under "solvent" containing azithromycin in a concentration as specified in TABLE 3 below under "conc (mg/ml)". The solid is filtrated off. The solvent of the filtrate is distilled off, e.g. by evaporation, to dryness. Anhydrous azithromycin in an amount (in gram) as specified in TABLE 3 below under "Yield wet (g)" (containing solvent as specified in TABLE 3 below under "solvent") with a content of azithromycin (in %) calculated on anhydrous basis as specified in TABLE 3 below under "Content wet" is obtained and dried at ca. 60° C. for ca. 14 hours. Azithromycin in anhydrous form is obtained containing an amount of azithromycin (in %) calculated on anhydrous basis as specified in TABLE 3 under "Content dry" below and having a water content (in %) as specified in TABLE 3 under "Content water".

TABLE 3

| Example | Solvent | Conc (mg/ml) | Yield wet (g) | Content wet | Content dry | Content water |
|---|---|---|---|---|---|---|
| 11 | ethyl acetate | 30 | 3.15 | 90.5% | 97.8 | 0.53 |
| 12 | isopropyl acetate | 30 | 3.33 | 89.9% | 97.8% | 0.53 |
| 13 | n-butyl acetate | 30 | 3.28 | 89.5% | 97.8% | 0.53 |
| 14 | acetone | 30 | 3.18 | 95.5% | 96.6 | 0.75 |
| 15 | methyl-isobutyl ketone | 30 | 3.22 | 89% | 96.6 | 0.75 |
| 16 | iso-propanol | 30 | 3.32 | 92% | 97.7 | 0.55 |
| 17 | ethanol | 30 | 3.0 | — | 96.1 | 0.56 |
| 18 | methanol | 30 | 3.61 | — | 97.4 | 0.61 |

The water content is maintained under normal environment air humidity conditions, for at least 24 hours, e.g. for several weeks.

What is claimed is:

1. In the process for the production of azithromycins by methylation of the nitrogen atom in position 9 of the ring structure in 9-deoxo-9a-aza-9a-homoerythromycins in the presence of formaldehyde and in the presence of a reducing agent, the improvement comprising that methylation is carried out in a non-halogenated solvent which is ethyl acetate, isopropyl acetate or butyl acetate.

2. The process according to claim 1 in the production of azithromycin of formula

I

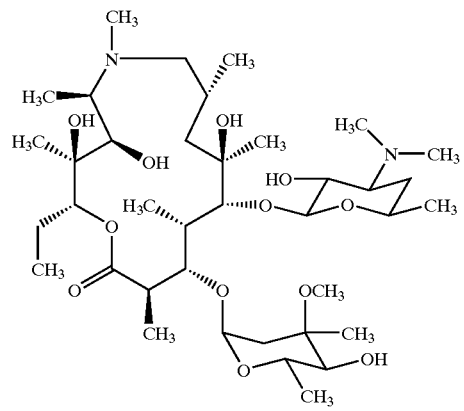

comprising converting a 9-deoxo-9a-aza-9a-methyl-9a-homoerithromycin A into a formula 1.

3. The process according to claim 2 wherein a 9-deoxo-9a-aza-9a-homoerythromycin is a compound of formula

II

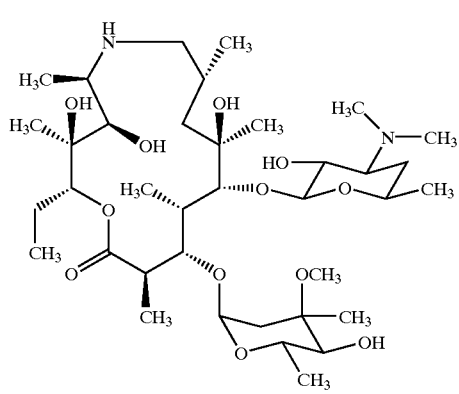

* * * * *

UNITED STATES PATENT AND TRADEMARK OFFICE
CERTIFICATE OF CORRECTION

PATENT NO.    : 6,420,537 B1                                    Page 1 of 1
DATED         : July 16, 2002
INVENTOR(S)   : Bosch et al.

It is certified that error appears in the above-identified patent and that said Letters Patent is hereby corrected as shown below:

Column 10,
Line 32, should read:
-- homoerithromycin A into a compound of formula 1. --

Signed and Sealed this

Twenty-ninth Day of July, 2003

JAMES E. ROGAN
*Director of the United States Patent and Trademark Office*